United States Patent [19]

Moody et al.

[11] Patent Number: 5,844,115

[45] Date of Patent: Dec. 1, 1998

[54] ALKOXYLATION PROCESS

[75] Inventors: Keith Moody, Watsonia North; Rodney W Parr, Doncaster; David Parris, Parkville; Kenneth R Deutscher, Sunbury; Esennur E Tasdelen, Mulgrave, all of Australia

[73] Assignee: ICI Australia Operations Proprietary Limited, Melbourne, Australia

[21] Appl. No.: 325,399

[22] PCT Filed: Apr. 23, 1993

[86] PCT No.: PCT/AU93/00174

§ 371 Date: Feb. 13, 1995

§ 102(e) Date: Feb. 13, 1995

[87] PCT Pub. No.: WO93/22266

PCT Pub. Date: Nov. 11, 1993

[30] Foreign Application Priority Data

Apr. 24, 1992 [AU] Australia ................................. PL 2031
Jan. 22, 1993 [AU] Australia ................................. PL 6930

[51] Int. Cl.[6] .................................................. C07C 43/11
[52] U.S. Cl. .......................... 568/618; 568/678; 568/679; 568/680
[58] Field of Search .................... 568/618, 619, 568/678, 679, 680

[56] References Cited

U.S. PATENT DOCUMENTS 4,404,408  9/1983  Wirth ........................................ 568/619
4,727,199  2/1988  King ........................................ 568/618

FOREIGN PATENT DOCUMENTS 1246617  1/1988  Canada .

OTHER PUBLICATIONS

Derwent Abstract Accession No. 404577/23, Class E17, JP,A,52051307, Apr. 25, 1977.

Derwent Abstract Accession No. 09042 E/02, Class E19, JP,A,56166137, Dec. 21, 1981.

Primary Examiner—José G. Dees
Assistant Examiner—Dwayne C. Jones
Attorney, Agent, or Firm—Cushman Darby & Cushman IP Group of Pillsbury Madison & Sutro, LLP

[57] ABSTRACT

Active hydrogen containing organic compounds, for example alcohols, thiols, phenols, thiophenols, carboxylic acids, amides and amines, are alkoxylated, for example, ethoxylated, using catalysts comprising a salt of a Group IIa or Group Ia element and an oxyacid of at least one element chosen from Group IVb, Group Vb or Group VIb, for example, lanthanum titanate, barium titanium, barium strontium titanate, yttrium titanate, lanthanum zirconate, barium zirconate, lanthanum hafnate, barium strontium titanate zirconate and neodymium titanate. The catalyst provide narrow distribution of alkoxylation species and efficient reaction rates.

25 Claims, 10 Drawing Sheets

ALKOXYLATION PROCESS

FIELD OF THE INVENTION

The present invention relates to the preparation of alkoxylation products by the catalysed condensation reaction of epoxides (alkylene oxides) and organic compounds having at least one active hydrogen.

DESCRIPTION OF THE PRIOR ART

A wide variety of alkoxylation products prepared by the condensation reaction of alkylene oxides with organic compounds having at least one active hydrogen are of industrial significance. The products of condensation of an alkylene oxide, and particularly ethylene oxide or propylene oxide or mixtures thereof, and an alcohol or a phenol are well known surface active agents. Other condensation products find application as solvents, and functional fluids. Such alkoxylation products are conventionally prepared by the reaction of at least one active hydrogen compound with an alkylene oxide (epoxide) in the presence of an alkaline or acidic catalyst. The average oxyalkylene chain length of such alkoxylation products depends on the mole ratio of epoxide to active hydrogen containing organic compound used and the reaction results in a mixture of different compounds having a range of oxyalkylene chain lengths and hence molecular weights.

It has long been recognised as desirable to control the molecular weight distribution of alkoxylates in order to be able to take best advantage of the properties of alkoxylates with specific alkylene oxide chain lengths. Acidic catalysts are known to tend to give narrower molecular weight distributions than alkaline catalysts but also promote side reactions which lead to the formation of undesired by-products. The commonly used alkaline catalysts are known to give broad molecular weight distribution but few by-products and are generally the alkoxylation catalysts used in industry today. Such catalysts include the alkali metal hydroxides and alkoxides and in particular sodium and potassium hydroxide.

In recent years much attention has been focused on developing catalysts which are as efficient as the alkali metal hydroxides but give products with narrow molecular weight distribution. U.S. Pat. No. 4,453,023 describes a process which employs a catalyst comprising a barium compound and a promoter selected from various oxides and acids of phosphorus, carbon dioxide and oxalic acid. International patent application publication number WO85/00365 describes use of an alkoxylation catalyst comprising the reaction product of calcium oxide or calcium hydroxide and an inorganic oxyacid derivative with an organic compound. European patent publication numbers 361616 to 361620 describe alkoxylation catalysts prepared by reacting various Group IIA, IIIB and other metal sources with an organic activator to give a composition which is further reacted with a di or poly-valent metal or metal containing compound such as divalent or polyvalent oxyacid salts. European patent publication number 361621 describes the use of calcium sulphate as an alkoxylation catalyst. European patent publication number 398450 describes the use of barium phosphate as an alkoxylation catalyst.

SUMMARY OF THE INVENTION

It is now been found that salts of the Group Ia, IIa and the rare earth elements and the oxyacids of the Group Ivb, Vb and VIb elements may be used as catalysts in alkoxylation reactions and that these catalysts give the desired features of an narrow distribution of alkoxylation species and efficient reaction rates.

Accordingly the invention provides a process for the alkoxylation of organic compounds containing at least one active hydrogen which process comprises reacting said organic compound with an alkylene oxide in the presence of a catalytically effective amount of a catalyst comprising the salt of at least one element chosen from a Group Ia or Group IIa or rare earth element and an oxy acid of at least one element chosen from a Group IVb, Group Vb or Group VIb element or mixtures thereof.

DESCRIPTION OF PREFERRED EMBODIMENTS

Preferably the catalysts used in the process of the invention are selected from compounds of the general formula I:

$$M_m(XO_n) \qquad \qquad I$$

wherein:
M is selected from the group consisting of Li, Na, K, Mg, Ca, Sr, Ba, Sc, Y, La, Ce and Nd and mixtures thereof;
X is selected from the group consisting of Ti, Zr, Hf, Nb, Mo, W and mixtures thereof;
m and n are selected to satisfy valency requirements, n being typically 2.0 to 6.0 and m being typically 0.2 to 2.0.

Preferred values for M include K, Ca, Sr, Ba, La, Y and Nd and mixtures thereof.

Preferred values for X include Ti, Zr, Hf, Mo, Nb and mixtures thereof.

Preferred compounds for formula I for use as catalysts in the process of the present invention include barium titanate, barium zirconate, strontium titanate, strontium zirconate, barium strontium titanate, lanthanum titanate, potassium lanthanum titanate, yttrium titanate, lanthanum zirconate, lanthanum hafnate, barium strontium titanate zirconate, barium niobate, lanthanum molybdate and neodymium titanate and calcium titanate.

More preferred compounds of formula I for use as catalysts in the process of the present invention include lanthanum titanate, barium titanate, barium strontium titanate, yttrium titanate, lanthanum zirconate, barium zirconate, lanthanum hafnate, barium strontium titanate zirconate and neodymium titanate.

As used herein the term "rare earth element" includes scandium, yttrium, lanthanum and elements of atomic numbers 58 through to 71 (the lanthanides).

The process of the present invention may be applied to alkoxylation using a range of alkylene oxides. Examples of alkylene oxides include ethylene oxide, propylene oxide, the butylene oxides, glycidol, epichlorohydrin, cyclohexene oxide, cyclopentene oxide and styrene oxide. The process of the invention is particularly useful in ethoxylation reactions using ethylene oxide and propoxylation reactions using propylene oxide and alkoxylation using mixed ethylene and propylene oxides.

The process of the present invention may be used in the alkoxylation of a wide range of organic compounds containing reactive hydrogen. Examples of such compounds include alcohols, thiols, phenols, thiophenols, carboxylic acids, amides and amines. Examples of alcohols which may be alkoxylated using the process of the present invention include primary and secondary $C_1$–$C_{30}$ straight and branch chain alcohols, cycloaliphatic alcohols, glycols, polyethylene glycols, polypropylene glycols, and polyhydric alcohols such as pentaerythritol and glycerol.

Alcohols and phenols, including alkyl substituted phenols, are preferred organic compounds containing reactive hydrogen which may be alkoxylated using the process of the present invention. Preferred alcohols include $C_1$–$C_{30}$ alcohols with $C_6$–$C_{20}$ alcohols amongst those most preferred. Preferred phenols include phenol and $C_1$–$C_{20}$ alkyl substituted phenols such as, for example, 4-nonylphenol and 4-decylphenol.

The amount of catalyst used in the process of the present invention depends to a large extent on the specific catalyst used and the organic compound containing reactive hydrogen and the alkylene oxide which are being reacted. Hence the amount of catalyst used is that amount which is catalytically effective in carrying out the alkoxylation reaction at the rate and with the selectivity desired. Typically the catalyst level may vary in the range of from 10 ppm to 10 percent by weight based on the weight of the organic compound containing reactive hydrogen. Preferably the catalyst is in the range of from 0.1 to 10% by weight of the organic compound containing reactive hydrogen.

In a preferred embodiment the process of the current invention for alkoxylation of organic compounds comprises the steps of;
 adding a catalyst to the organic compound containing at least one active hydrogen,
 heating and pressurising the reactor containing said organic compound,
 supplying alkylene oxide to said organic compound and catalyst at a process temperature of between 50° and 250° C. and at a process pressure of between 300 and 700 kPa and isolating the alkoxylation products.

The temperature which the process of the present invention is carried out will depend upon a number a factors including the heating and cooling facilities available in the reaction vessel and the pressure at which the reaction vessel may be operated. However, in general, a temperature in the range of from 50° to 250° C. is satisfactory and a temperature in the range of from 80° to 200° C. may be preferred.

The pressure at which the process of the present invention is carried out will depend to a large extent on the alkylene oxide used and the temperature at which the reaction is carried out. However, preferably the process of the present invention is carried out at a pressure above atmospheric pressure. In practice a reaction pressure of between 300 kPa and 700 kPa with an alkylene oxide partial pressure of between 100 and 500 kPa has been found to be suitable.

The reaction time required for the process of the present invention is dependent upon the nature of the reactive hydrogen compound and the nature of the alkylene oxide used, the reaction temperature and pressure and the catalyst and quantity of the catalyst used. In practice, reaction times may vary from 15 minutes to approximately 20 hours. Surprisingly, it has been found that certain catalysts used in the process of the present invention, including barium strontium titanate, provide a reaction rate which is similar to the reaction rate obtained with potassium hydroxide as well as producing narrow molecular weight distribution products.

The catalysts used in the present invention may be in the form of finely divided solids. Therefore, if desired, after the reaction has been completed and the product cooled, the catalyst may be recovered from the final product by any means suitable for the removal of finely divided solid from a reaction mixture. For example, depending on the size of the finely divided solid and the viscosity of the product, the catalyst may be removed by filtration, centrifugation, extraction or suitable like means.

It should be noted, that although not essential for the process of the present invention, the catalyst used for the process of the present invention may also contain other components including impurities resulting from the preparation of the catalyst and introduced components which may be added to promote or modify catalyst activity and/or selectivity.

Surprisingly, the process of the present invention provides molecular weight distributions for both lower and higher alkoxylates that are narrower than those which would be expected from alkoxylation reactions using conventional alkali metal hydroxide catalysis.

EXAMPLES

The invention is now illustrated by, but not limited to, the following Examples.

EXAMPLE 1

Barium titanate was prepared by the following procedure. A solution of tetrabutyltitanate (30.6 grams, 0.0899 moles) in isopropanol (150 ml) was added dropwise over 45 minutes to a well stirred solution of barium hydroxide (31.5 grams of $Ba(OH)_2 \cdot 8H_2O$, 0.100 moles) in deionised water (1000 ml) at 50°–60° C. The resulting mixture was heated at 50°–60° C. for an additional 20 minutes, the white precipitate allowed to settle and the supernatant liquid decanted. The precipitate was washed with deionised water several times and dried at 400° C. for 3 hours.

An alkoxylation process in accordance with the invention was conducted under the following procedures. The alkylene oxide reactant for this process embodiment consisted of ethylene oxide and the active hydrogen containing reactant consisted of NACOL-10-99 Alcohol (NACOL is a registered trade mark of Condea Chemie) characterised as a primary, linear alkanol having ten carbon atoms (>99%).

Figure 1:
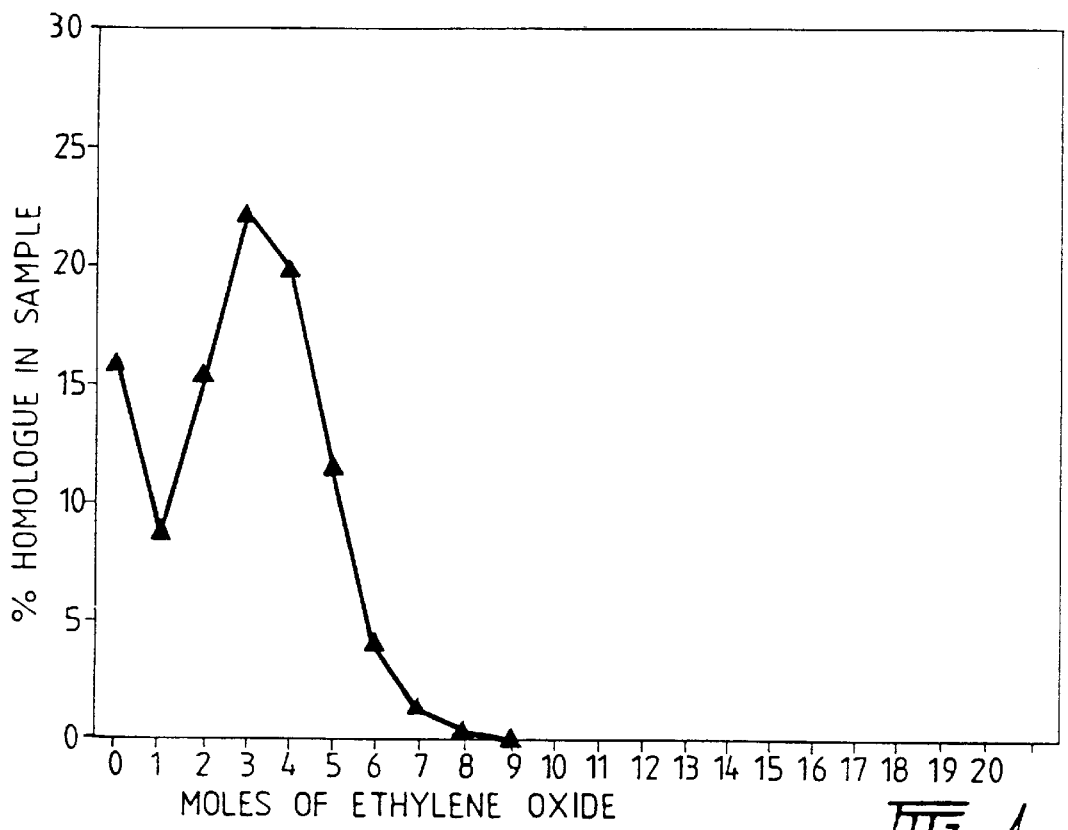
FIGS. 1–20 are graphs illustrating ethylene oxide adduct distribution of products obtained according to the following examples demonstrating the advantages of the invention.

Initially, 5.84 grams of the barium titanate prepared as described above was added to 254 grams of NACOL-10-99 Alcohol, and the mixture was transferred to a 2 liter autoclave reactor maintained under nitrogen atmosphere. The autoclave and its contents were then heated at 110° C. under vacuum for one hour to drive off water. The mixture was then heated to 150° C. and the autoclave pressurised to 40 kPa with nitrogen. Ethylene oxide was then introduced into the reactor to a total pressure of 400 kPa. Alkoxylation (ethoxylation) commenced immediately. Additional ethylene oxide was supplied on demand to maintain a pressure of 400 kPa and temperature maintained between 150° to 160° C. A total of 190 grams of ethylene oxide was taken up over a period of 35 minutes. The reactor was maintained at temperature for an additional 30 minutes to consume unreacted ethylene oxide. The product was analysed by GLC techniques and found to have an average adduct number of 2.8. The ethylene oxide adduct distribution of the product is presented in FIG. 1.

Figure 2:
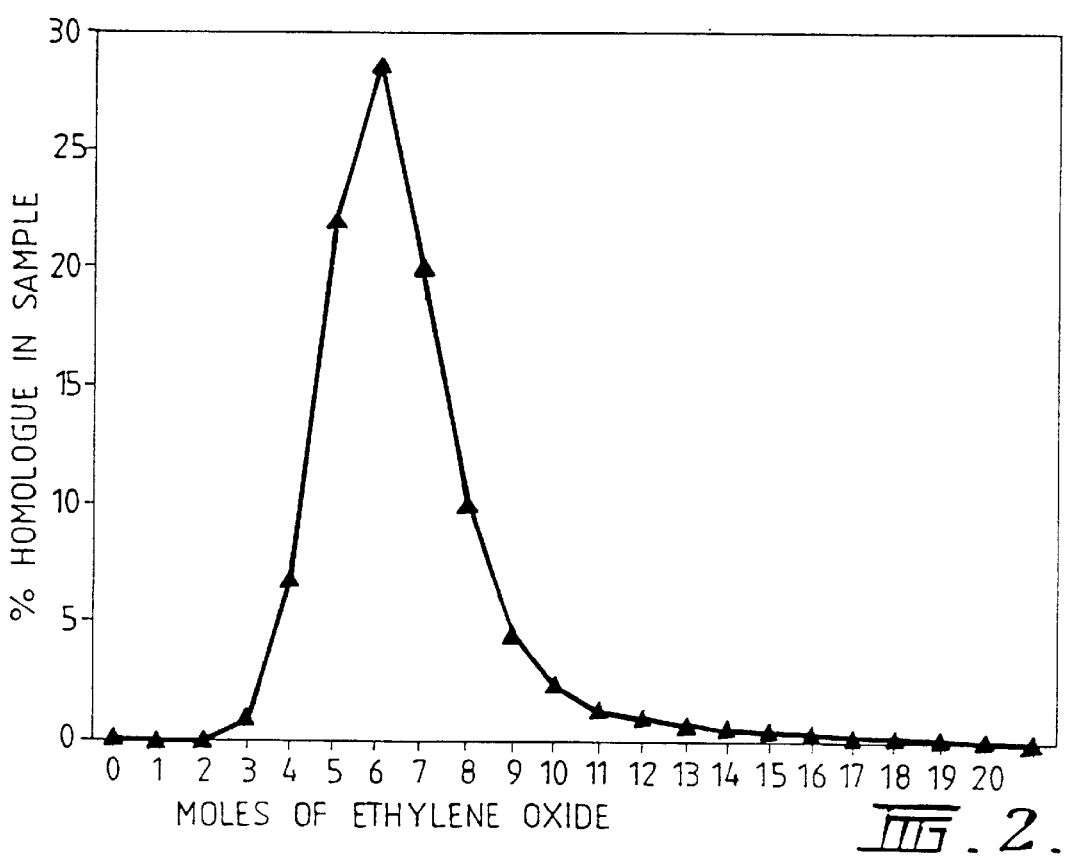

Further ethoxylation of this product (266 grams) was carried out following the above general procedure. A total of 200 grams of ethylene oxide was taken up over a period of 1.6 hours. The reactor was maintained at temperature for an additional 1 hour to consume unreacted ethylene oxide. The product was analysed by GLC techniques to have an average adduct number of 6.6. The ethylene oxide adduct distribution of the product is presented in FIG. 2.

EXAMPLE 2

Barium zirconate was prepared by the following procedure. A solution of tetrabutylzirconate (31.0 grams of $Zr(OBu)_4 \cdot BuOH$, 0.0676 moles) in isopropanol (130 ml) was added dropwise over 30 minutes to a well-stirred solution of barium hydroxide (23.7 grams of $Ba(OH)_2 \cdot 8H_2O$, 0.0742 mol) in deionised water (600 ml) at 57°–60° C. The resulting mixture was heated at 59° C. for an additional 1.5 hours, then cooled to 20° C. and filtered. The white filter cake was washed with deionised water and dried at 200° C. for 3 hours.

Figure 3:
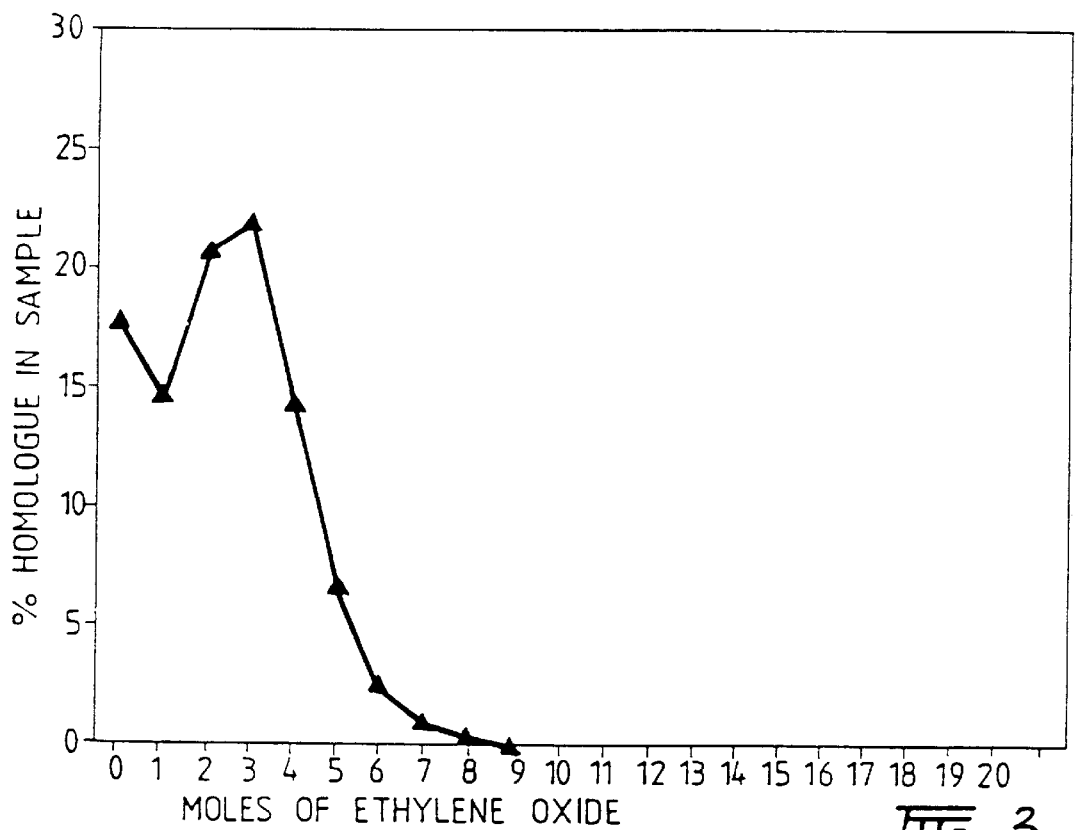

An alkoxylation process in accordance with the invention was conducted under the same general procedures described for Example 1, using as alkoxylation catalyst the barium zirconate prepared as described above. A total of 249 grams of NACOL-10-99 Alcohol and 6.93 grams of barium zirconate were used. At a reaction temperature of 150°–160° C., a total of 180 grams of ethylene oxide was added over 5.3 hours. The product was analysed by GLC techniques and found to have an average adduct number of 2.4. The ethylene oxide adduct distribution of the product is presented in FIG. 3.

EXAMPLE 3

Calcium titanate was prepared by the following procedure. A solution of tetrabutyltitanate (30.9 grams, 0.0907 moles) in isopropanol (150 ml) was added dropwise over one hour to a well stirred slurry of calcium hydroxide (7.86 grams of 95% $Ca(OH)_2$, 0.101 moles) in deionised water (1010 ml) at 51° C. The resulting mixture was heated at 51° C. for an additional 25 minutes, the white precipitate allowed to settle and the supernatant liquid decanted. The precipitate was washed with deionised water several times and dried at 400° C. for 17 hours.

Figure 4:
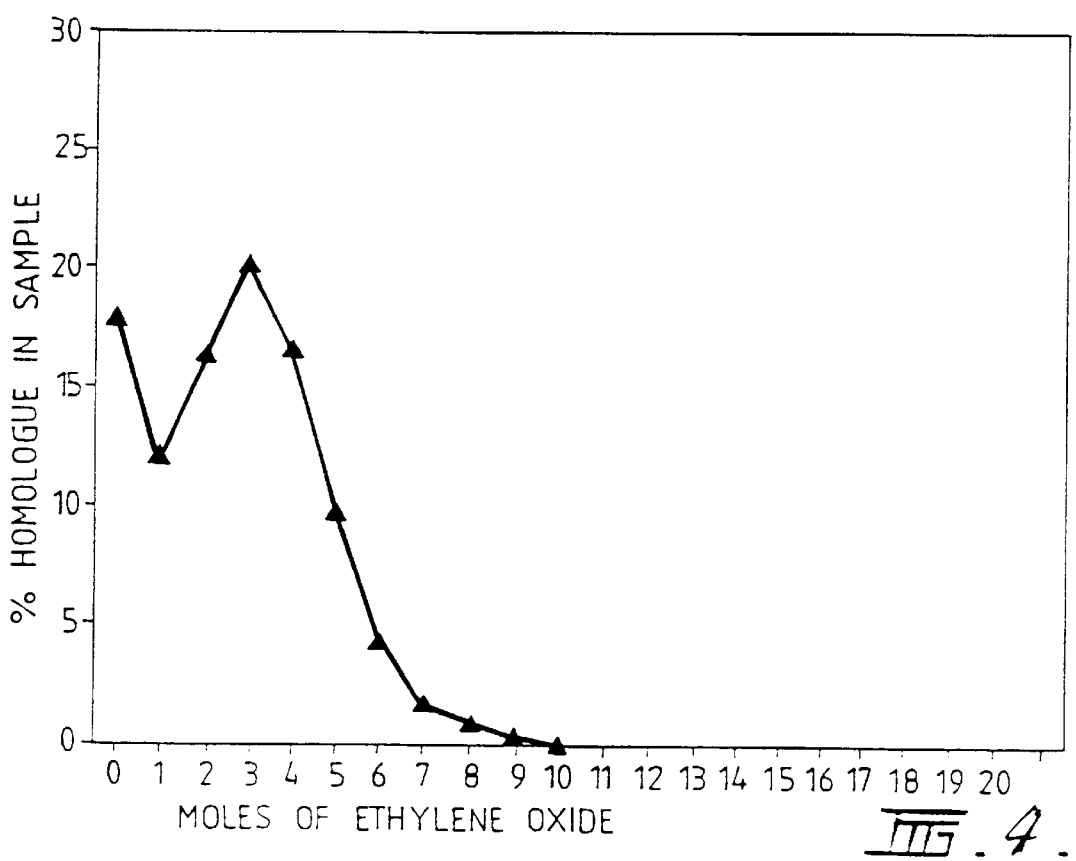

An alkoxylation process in accordance with the invention was conducted under the same general procedures described for Example 1, using as alkoxylation catalyst the calcium titanate prepared as described above. A total of 249 grams of NACOL-10-99 Alcohol and 2.40 grams of calcium titanate were used. At a reaction temperature of 150°–160° C., a total of 180 grams of ethylene oxide was added over 6 hours. The product was analysed by GLC techniques and found to have an average adduct number of 2.7. The ethylene oxide adduct distribution of the product is presented in FIG. 4.

EXAMPLE 4

Barium strontium titanate was prepared by the following procedure. A solution of tetrabutyltitanate (30.6 grams, 0.0899 moles) in isopropanol (150 ml) was added dropwise over 55 minutes to a well stirred solution of barium hydroxide (15.9 grams of $Ba(OH)_2 \cdot 8H_2O$, 0.0500 moles) and strontium hydroxide (13.7 grams of $Sr(OH)_2 \cdot 8H_2O$, 0.0500 moles) in deionised water (1000 ml) at 55°–58° C. The resulting mixture was heated at 57° C. for an additional one hour, the white precipitate allowed to settle and the supernatant liquid decanted. The precipitate was washed with deionised water several times and dried at 400° C. for 7 hours.

Figure 5:
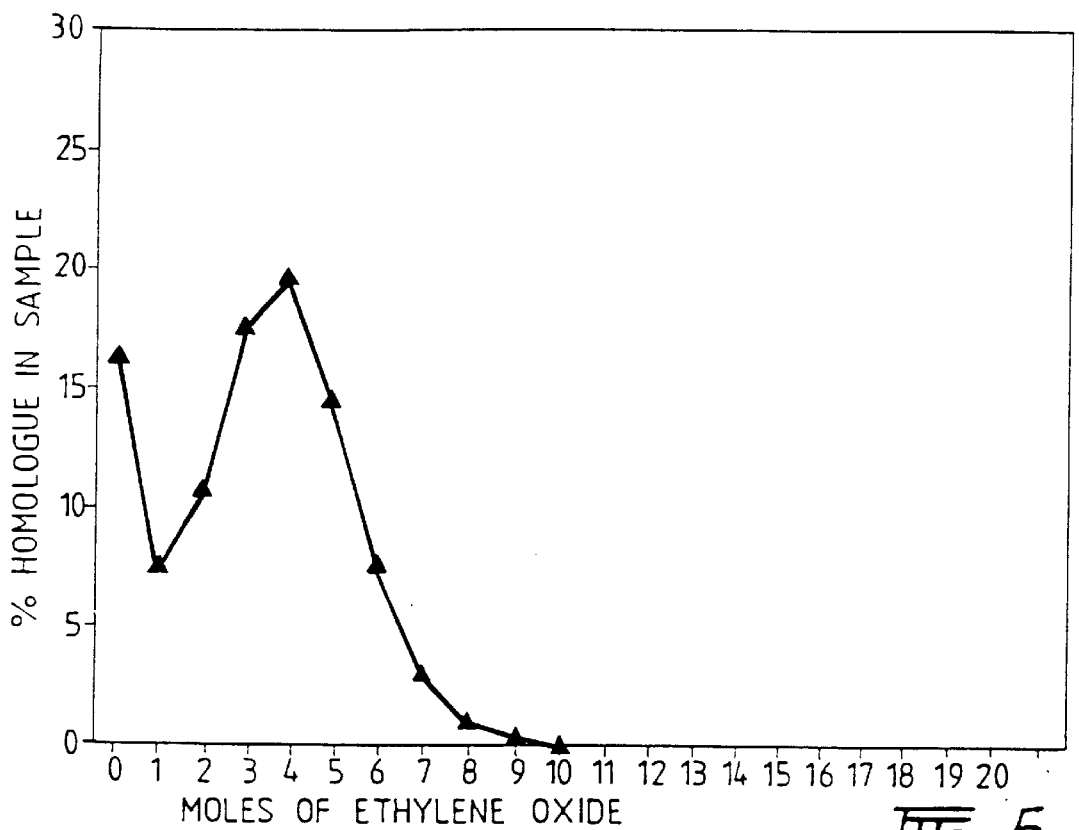
Figure 6:
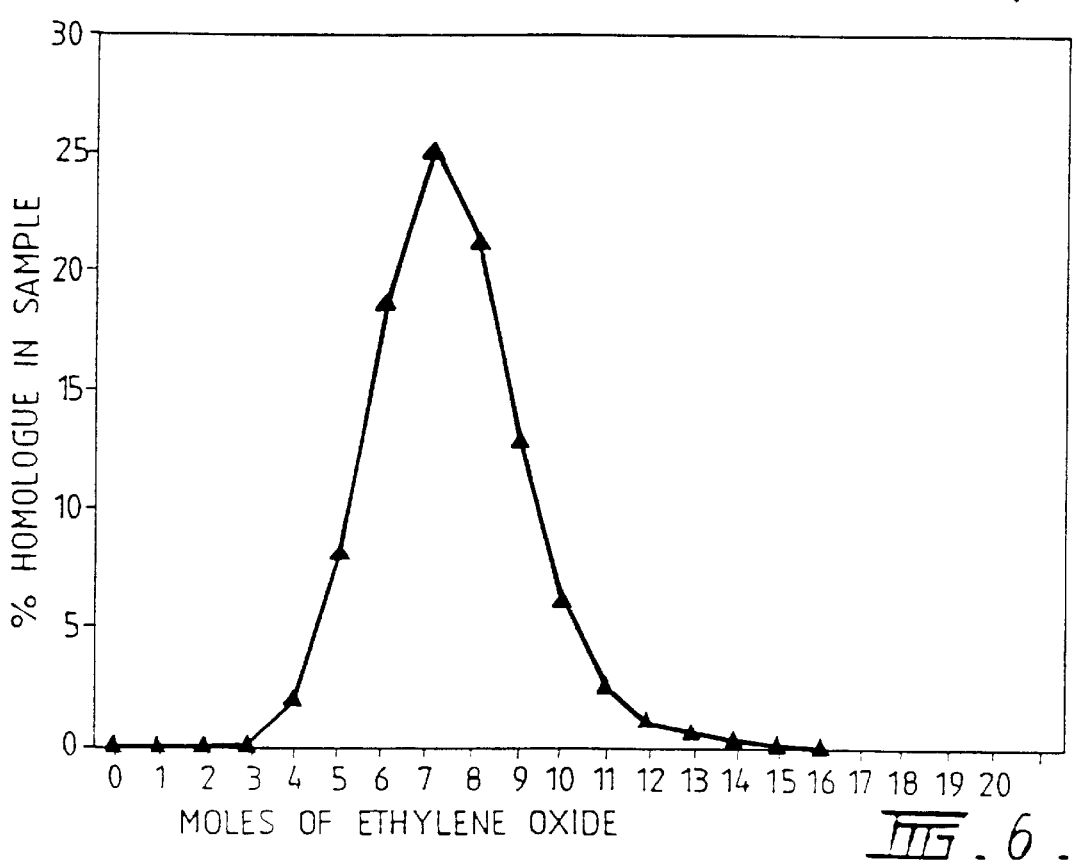

An alkoxylation process in accordance with the invention was conducted under the same general procedures described for Example 1, using as alkoxylation catalyst the barium strontium titanate prepared as described above. A total of 250 grams of NACOL-10-99 Alcohol and 5.22 grams of barium strontium titanate were used. At a reaction temperature of 150°–160° C., a total of 180 grams of ethylene oxide was taken up over 24 minutes. The product was analysed by GLC techniques and found to have an average adduct number of 3.2. The ethylene oxide adduct distribution of the product is presented in FIG. 5. Further ethoxylation of this product (219 grams) was carried out. A total of 170 grams of ethylene oxide was taken up over a period of 55 minutes. The product was analysed by GLC techniques to have an average adduct number of 7.5. The ethylene oxide adduct distribution of the product is presented in FIG. 6.

EXAMPLE 5

Strontium titanate was prepared by the following procedure. A solution of tetrabutyltitanate (30.6 grams, 0.0899 moles) in isopropanol (150 ml) was added over 1.5 hours to a well stirred solution of strontium hydroxide (27.4 grams of $Sr(OH)_2 \cdot 8H_2O$, 0.100 moles) in deionised water (1000 ml) at 53°–56° C.

The resulting mixture was heated at 55° C. for an additional 20 minutes, the white precipitate allowed to settle and the supernatant liquid decanted. The precipitate was washed with deionised water several times and dried at 400° C. for 15 hours.

Figure 7:
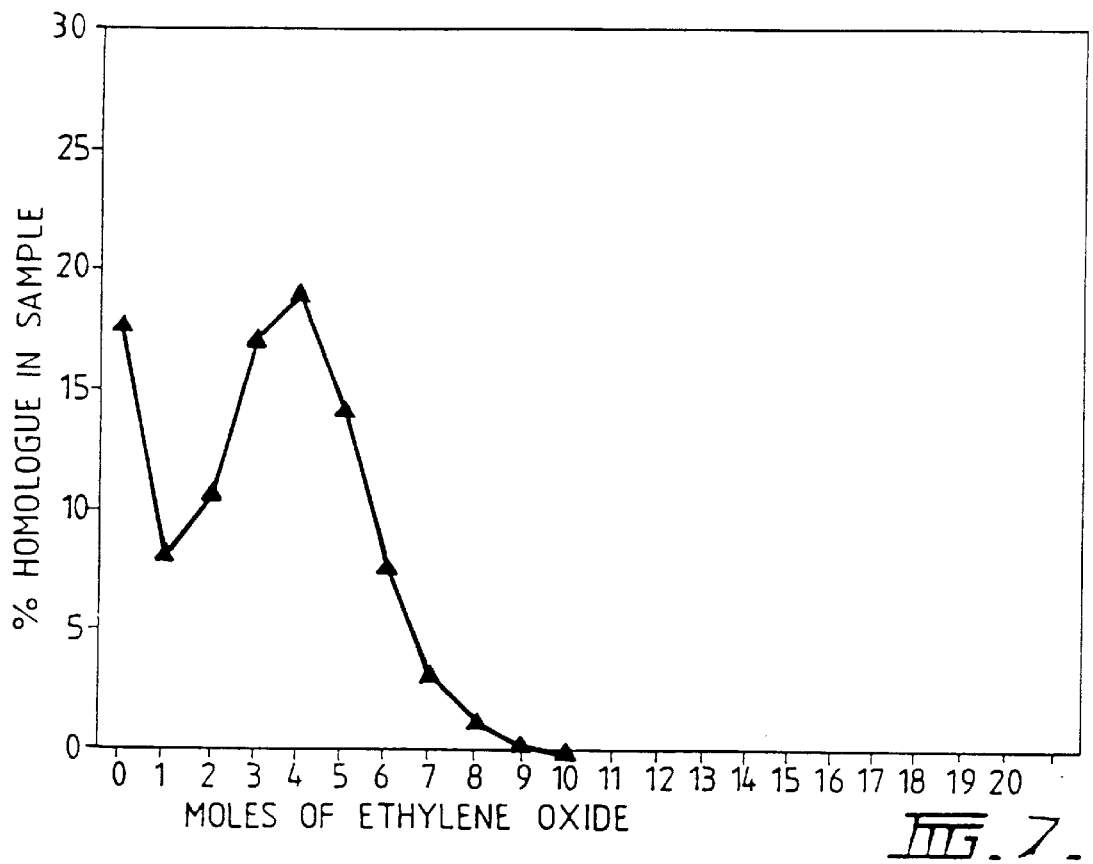

An alkoxylation process in accordance with the invention was conducted under the same general procedures described for Example 1, using as alkoxylation catalyst the strontium titanate prepared as described above. A total of 249 grams of NACOL-10-99 Alcohol and 4.59 grams of strontium titanate were used. At a reaction temperature of 150°–160° C., a total of 170 grams of ethylene oxide was taken up over 2 hours and 10 minutes. The product was analysed by GLC techniques and found to have an average adduct number of 3.1. The ethylene oxide adduct distribution of the product is presented in FIG. 7.

Figure 8:
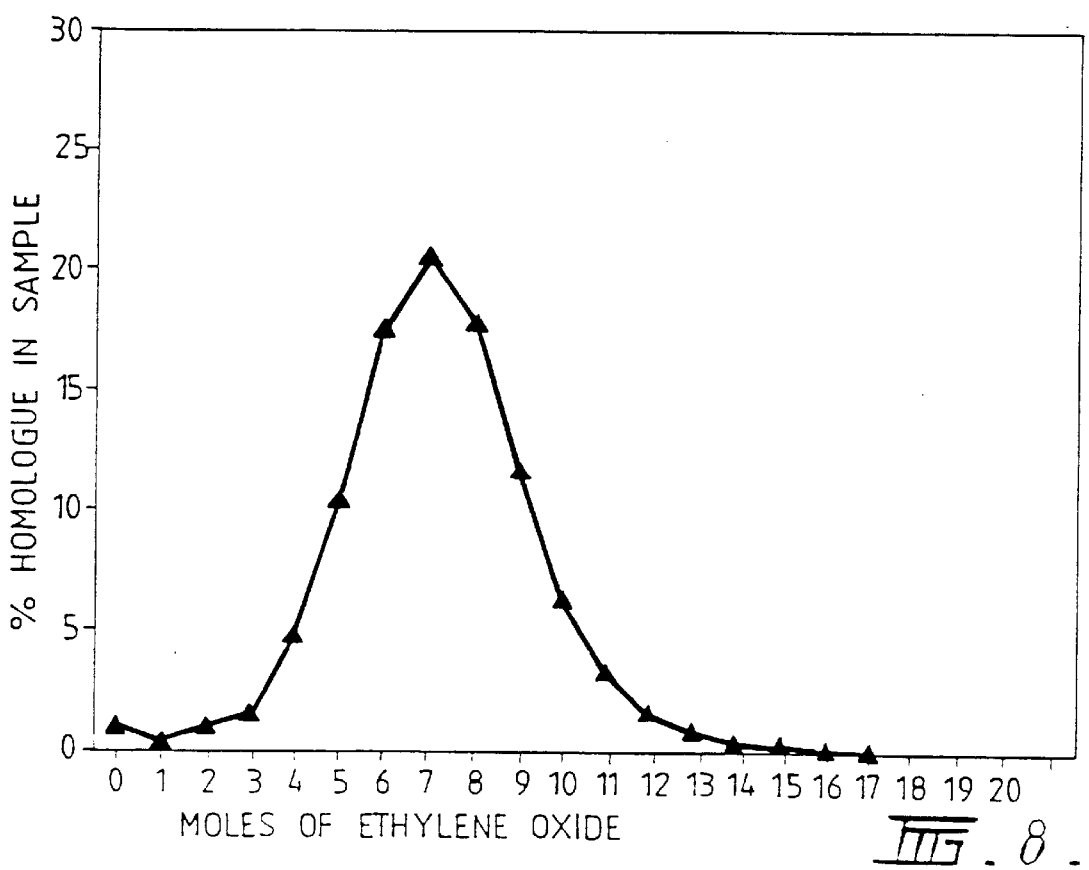

Further alkoxylation of this product (222 grams) was carried out. A total of 170 grams of ethylene oxide was taken up over a period of 5 hours and 40 minutes. The product was analysed by GLC techniques and found to have an average adduct number of 7.2. The ethylene oxide adduct distribution of the product is presented in FIG. 8.

EXAMPLE 6

Lanthanum titanate was prepared by the following procedure. Ammonia solution (30 ml, 28% w/w) was added to a vigorously stirred solution of lanthanum nitrate (26.6 grams of $La(NO_3)_3 \cdot 6H_2O$, 0.0614 moles) in deionised water (1000 ml) at 55° C. A solution of tetrabutyltitanate (20.5 grams, 0.0602 moles) in isopropanol (180 ml) was then added over two hours to the resulting mixture at 55°–58° C., whilst maintaining vigorous stirring.

The reaction mixture was then heated at 55° C. for an additional two hours, during which time high pH (~10) was maintained by addition of ammonia solution. The white precipitate was allowed to settle and the supernatant liquid decanted. The precipitate was washed with deionised water several times and dried at 400° C. for 19 hours.

Figure 11:
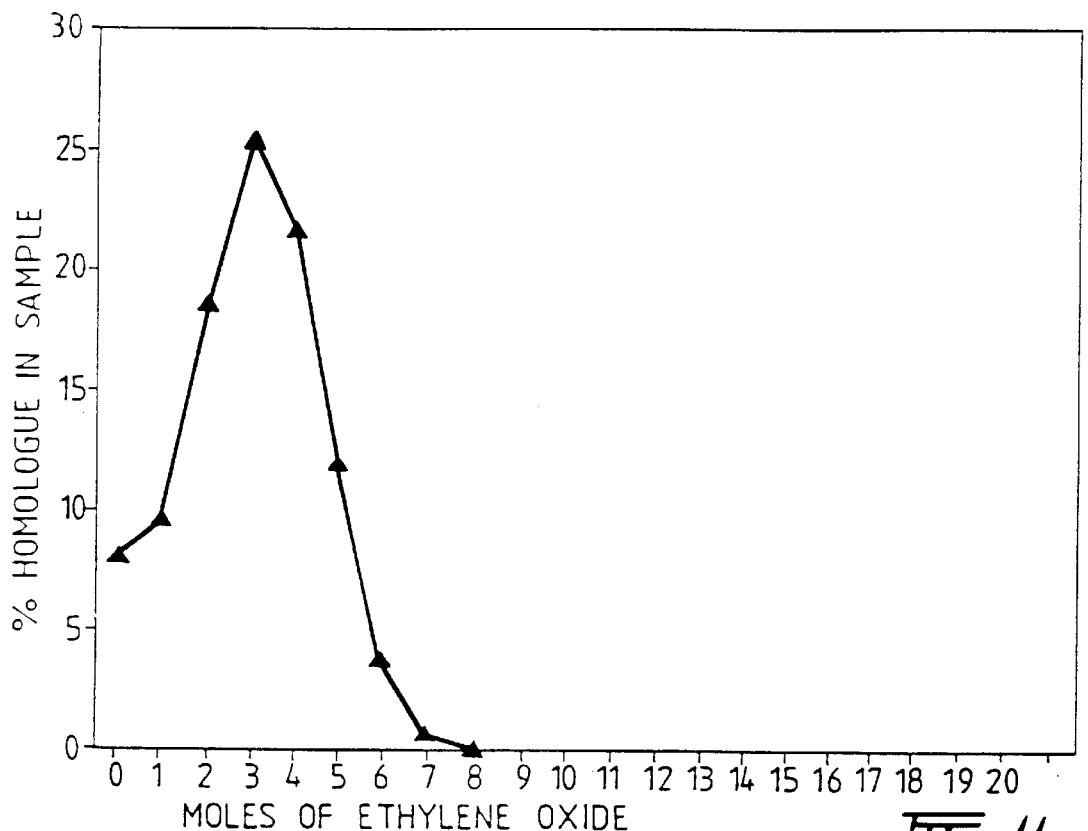

An alkoxylation process in accordance with the invention was conducted under the same general procedures described for Example 1, using as alkoxylation catalyst the lanthanum titanate prepared as described above. A total of 249 grams of NACOL-10-99 alcohol and 7.10 grams of lanthanum titanate were used. At a reaction temperature of 150°–160° C., a total of 210 grams of ethylene oxide was taken up over 125 minutes. The product was analysed by GLC techniques and found to have an average adduct number of 3.0. The ethylene oxide adduct distribution of the product is presented in FIG. 11.

Figure 12:
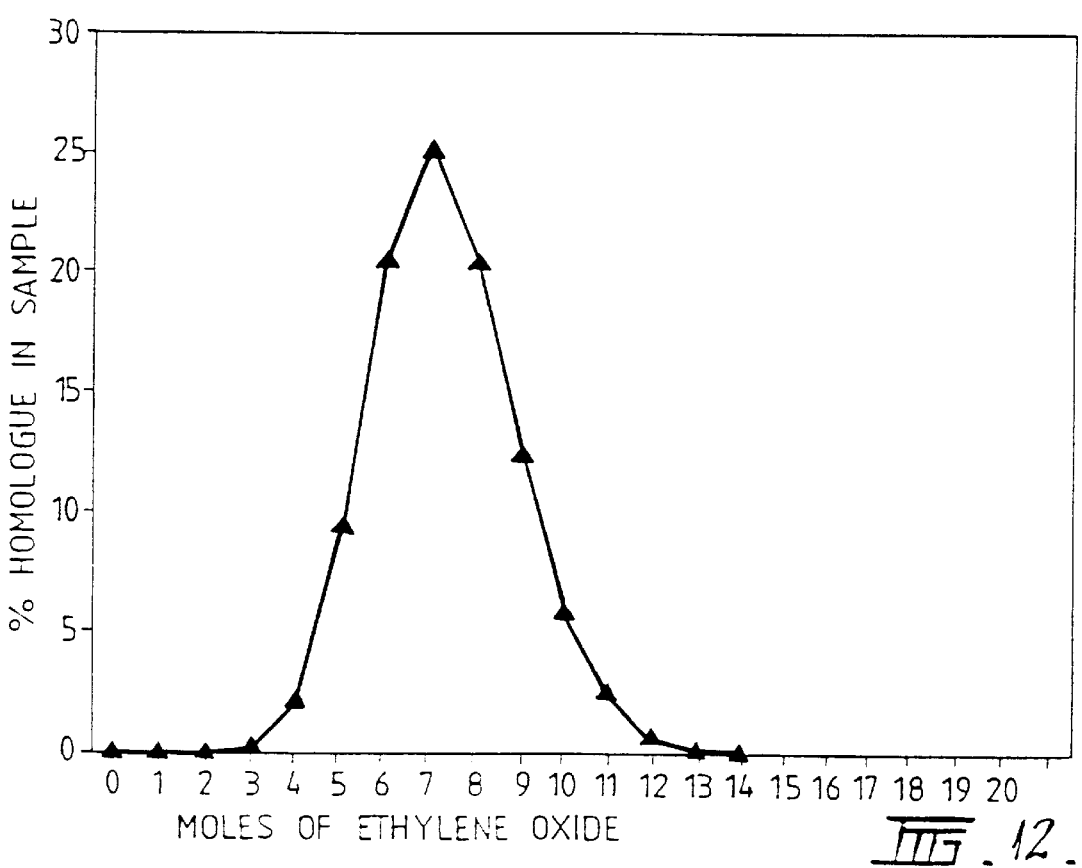

Further ethoxylation of this product (307 grams) was carried out. A total of 235 grams of ethylene oxide was taken up over a period of 115 minutes. The product was analysed by GLC techniques to have an average adduct number of 7.3. The ethylene oxide adduct distribution of the product is presented in FIG. 12.

EXAMPLES 6b AND 6c

Further examples of alkoxylations using lanthanum titanate catalysts are illustrated, following the procedures described in Example 6.

TABLE

Example 6b and 6c

| Example No | Molar Ratio La:Ti | Catalyst Drying Temp (°C.) | Alkoxylation Time h/mol EO |
|---|---|---|---|
| 6b | 27.5:72.5 | 400 | 0.3 |
| 6c | 27.5:72.5 | 300 | 0.2 |

EXAMPLE 7

Figure 13:
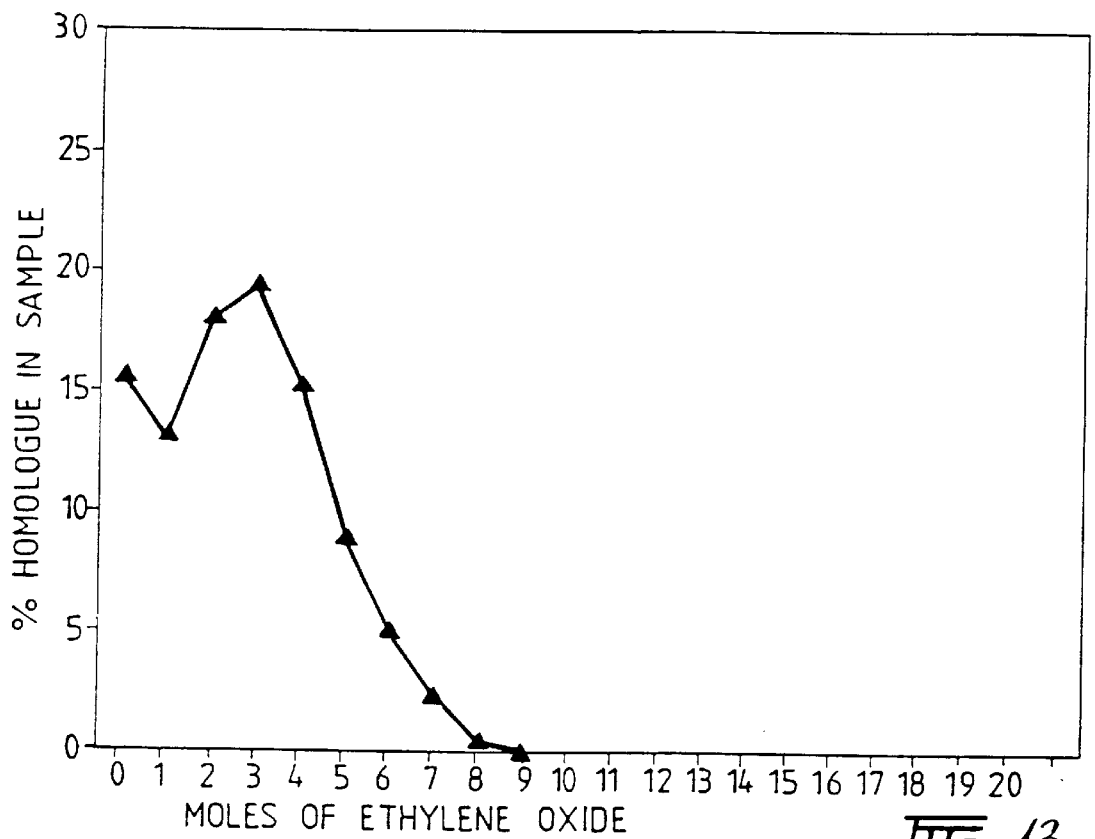

Potassium lanthanum titanate was prepared by the following procedure. A solution of tetrabutyltitante (42.9 grams, 0.126 moles) in isopropanol (160 ml) was added dropwise over 95 minutes to a vigorously stirred mixture of lanthanum nitrate (17.7 grams of $La(NO_3)_3.6H_2O$, 0.0409 moles) and potassium hydroxide (11.5 grams, 0.174 moles) in deionised water (1450 ml) at 53°–54° C. The resulting mixture was heated at 54° C. for an additional one hour, the white precipitate allowed to settle and the supernatant liquid decanted. The precipitate was washed with deionised water several times and dried at 400° C. for 5.5 hours. An alkoxylation process in accordance with the invention was conducted under the same general procedures described for Example 1, using as alkoxylation catalyst the potassium lanthanum titanate prepared as described above. A total of 250 grams of NACOL-10-99 alcohol and 4.13 grams of the potassium lanthanum titanate were used. At a reaction temperature of 150°–160° C., a total of 165 grams of ethylene oxide was added over 4 hours and 50 minutes. The product was analysed by GLC techniques and found to have an average adduct number of 2.7. The ethylene oxide adduct distribution of the product is presented in FIG. 13.

EXAMPLE 8

Yttrium titanate was prepared by the following procedure.

Yttrium oxide (8.00 grams of $Y_2O_3$, 0.0354 moles) was slowly dissolved in concentrated nitric acid (30 ml) and then heated gently whilst stirring to effect total dissolution. The solution was then boiled to almost dryness and the paste obtained was further dried in an oven at 200° C. for two hours. The solid obtained was cooled and dissolved in methanol (100 ml). A solution of titanium alkoxide (10.5 grams of $Ti(OR)_4$ where R=$^iPr$ (80%), R=$^nBu$ (20%), 0.0354 moles) was added to the methanolic yttrium solution.

This mixture was then added dropwise over 10 to 15 minutes to a vigorously stirred ammonia solution (35 ml of 28% w/w $NH_3$ in 500 ml of deionised water) at room temperature. The resulting suspension of white precipitate was boiled, cooled and then centrifuged. The white precipitate was resuspended in methanol (600 ml) which had been treated with 1–2 ml of ammonia solution and recentrifuged. The solid was dried initially in a vacuum oven then in a furnace at 400° C. for 3 hours.

Figure 14:
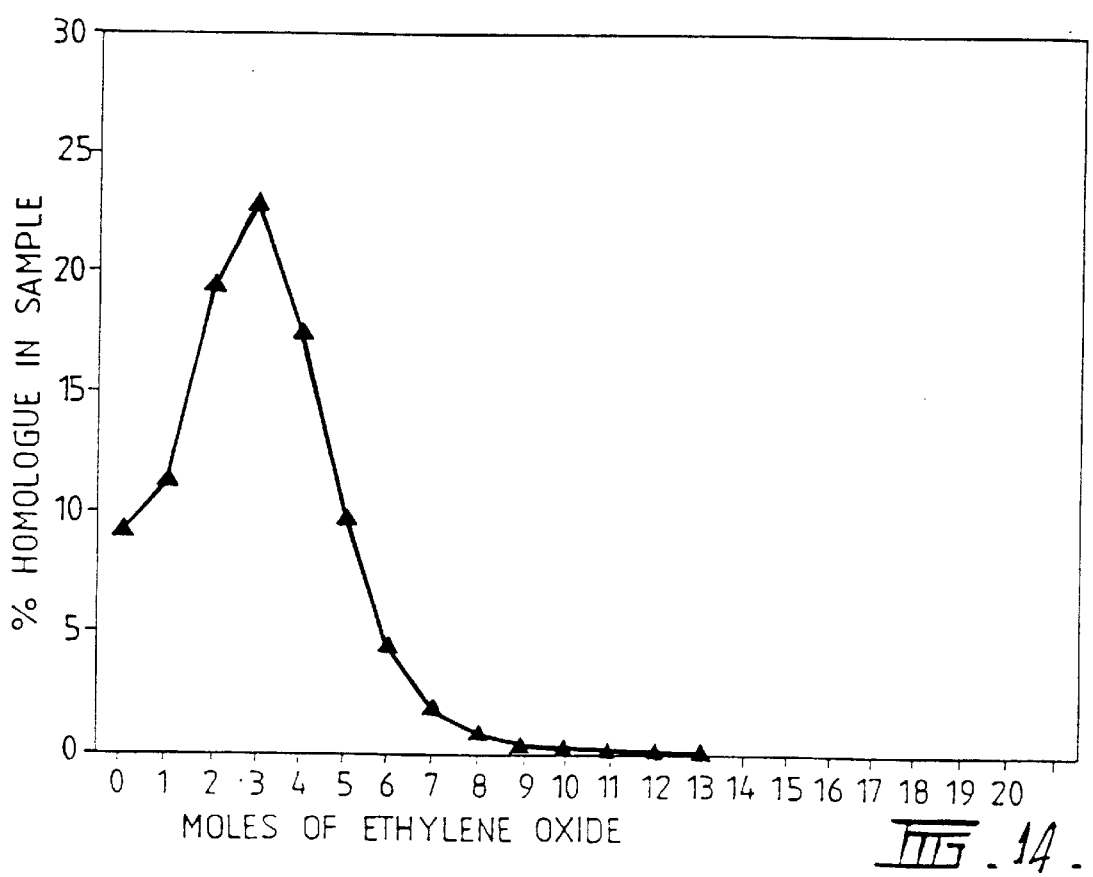

An alkoxylation process in accordance with the invention was conducted under the same general procedures described for Example 1, using as alkoxylation catalyst the yttrium titanate prepared as described above. A total of 262 grams of NACOL-10-99 alcohol and 6.00 grams of yttrium titanate were used. At a reaction temperature of 155°–160° C., a total of 230 grams of ethylene oxide was taken up over 1 hour and 45 minutes. The product was analysed by GLC techniques and found to have an average adduct number of 3.0. The ethylene oxide adduct distribution of the product is presented in FIG. 14.

Figure 15:
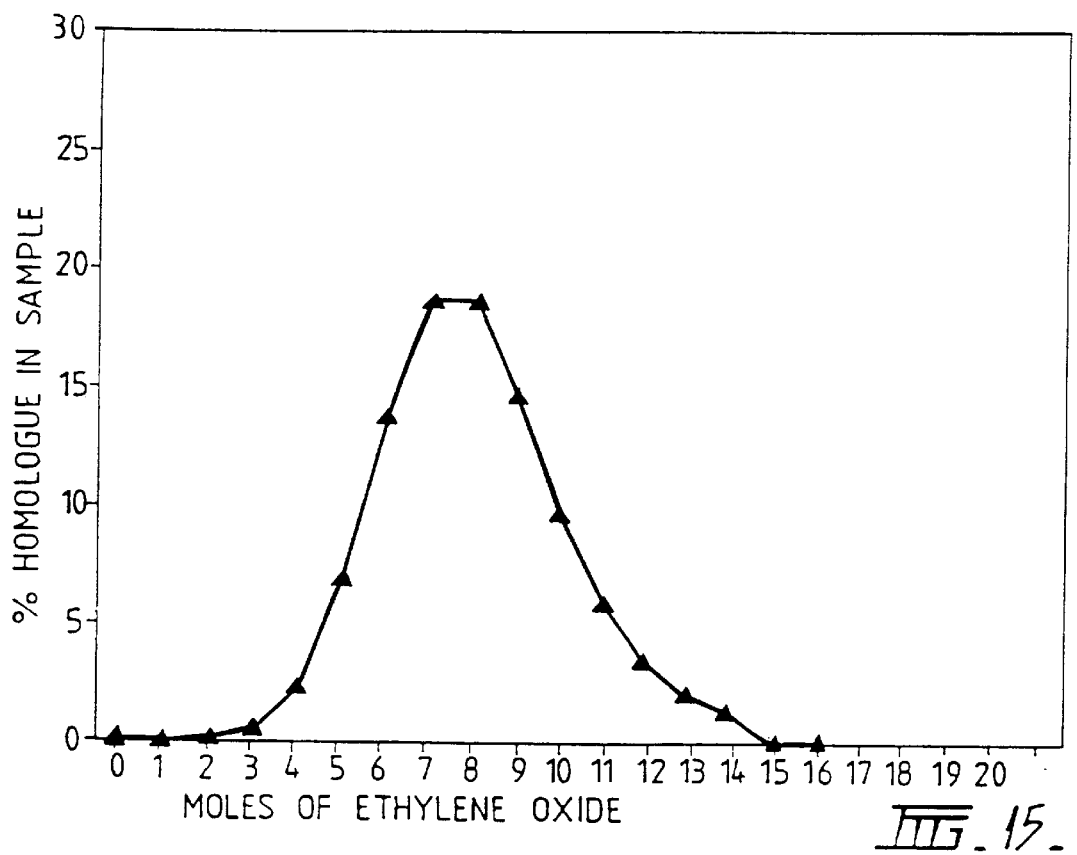

Further ethoxylation of this product (393 grams) was carried out. A total of 240 grams of ethylene oxide was taken up over a period of 2 hours. The product was analysed by GLC techniques to have an average adduct number of 8.0. The ethylene oxide adduct distribution of the product is presented in FIG. 15.

EXAMPLE 9

Lanthanum zirconate was prepared by the following procedure. Ammonia solution (90 ml, 28% w/w) was added to a vigorously stirred solution of lanthanum nitrate (44.3 grams of $La(NO_3)_3.6H_2O$, 0.102 moles) in deionised water (1030 ml) at 53° C. A solution of zirconium butoxide (45.8 grams of $Zr(OBu)_4.BuOH$, 0.100 moles) in isopropanol (200 ml) was then added over one hour to the resulting mixture at 50°–55° C., whilst maintaining vigorous stirring. The reaction mixture was then heated at 53° C. for an additional 2 hours, cooled and the white precipitate formed filtered and washed with deionised water. The precipitate was then dried at 400° C. for 16 hours.

Figure 16:
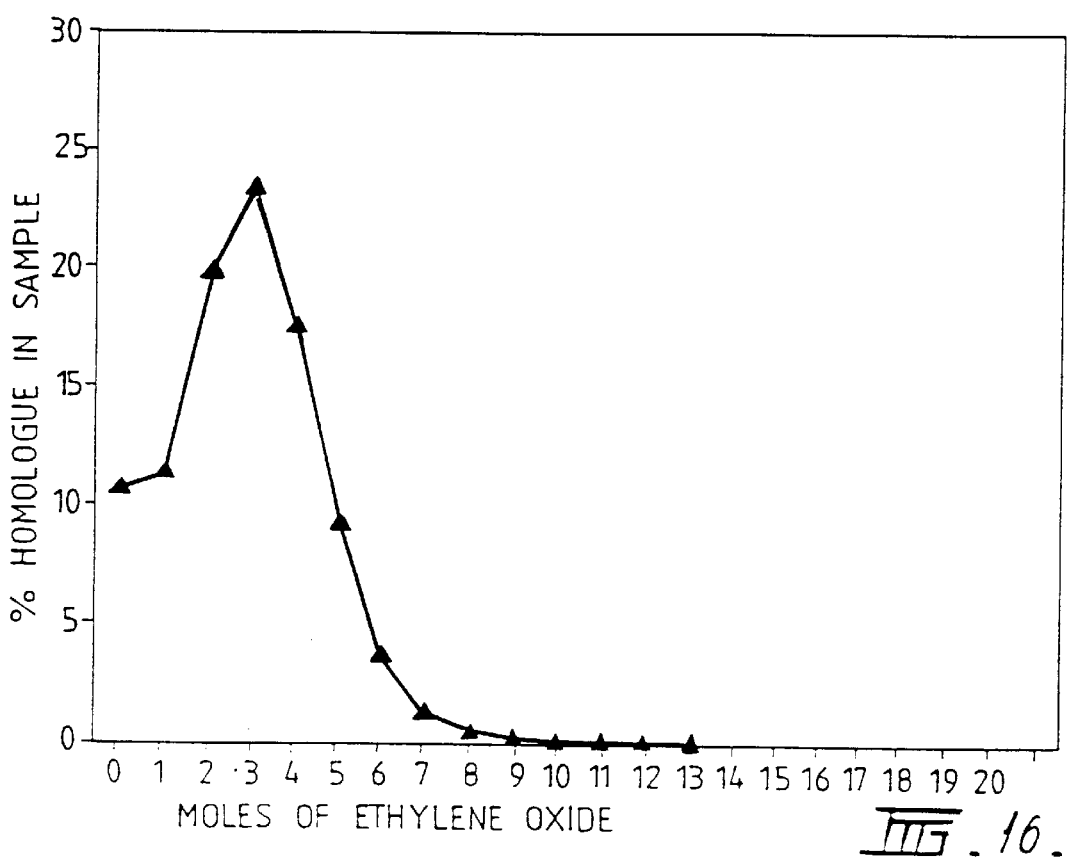

An alkoxylation process in accordance with the invention was conducted under the same general procedures described for Example 1, using as alkoxylation catalyst the lanthanum zirconate prepared as described above. A total of 249 grams of NACO1-10-99 alcohol and 8.74 grams of lanthanum zirconate were used. At a reaction temperature of 150°–160° C., a total of 210 grams of ethylene oxide was taken up over 8 hours. The product was analysed by GLC techniques and found to have an average adduct number of 2.8. The ethylene oxide adduct distribution of the product is presented in FIG. 16.

EXAMPLE 10

Lanthanum hafnate was prepared by the following procedure. Ammonia solution (90 ml, 28% w/w) was added to a vigorously stirred solution of lanthanum nitrate (26.6 grams of $La(NO_3)_3.6H_2O$, 0.0614 moles) in deionised water (1000 ml) at 53° C. A solution of hafnium chloride (19.6 grams of $HfCl_4$, 0.0600 moles) in methanol/isopropanol (3:2, 250 ml) was then added over one hour to the resulting mixture at 50°–55° C., whilst maintaining vigorous stirring. The reaction mixture was then heated at 53° C. for an additional 2 hours, cooled and the white precipitate formed filtered and washed with deionised water. The precipitate was then dried at 400° C. for 16 hours.

Figure 17:
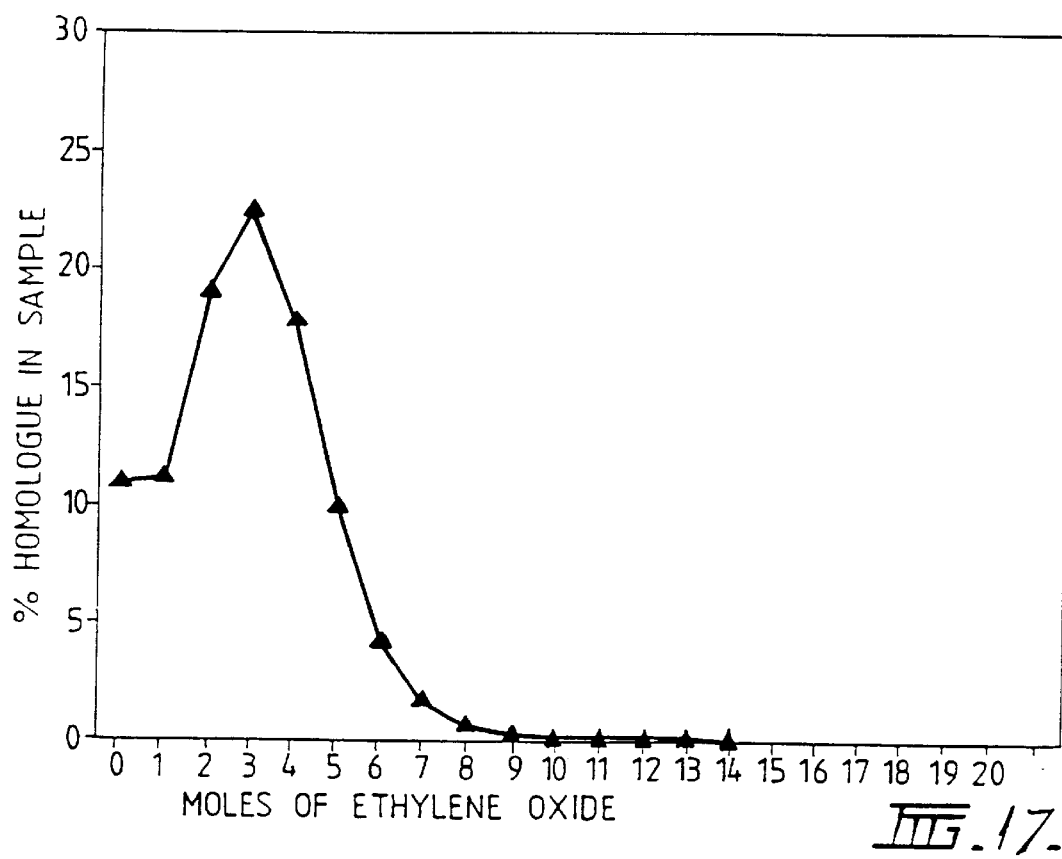

An alkoxylation process in accordance with the invention was conducted under the same general procedures described for Example 1, using as alkoxylation catalyst the lanthanum hafnate prepared as described above. A total of 250 grams of NACOL-10-99 alcohol and 12.0 grams of lanthanum hafnate were used. At a reaction temperature of 155°–160° C., a total of 210 grams of ethylene oxide was taken up over 6 hours. The product was analysed by GLC techniques and found to have an average adduct number of 2.9. The ethylene oxide adduct distribution of the product is presented in FIG. 17.

EXAMPLE 11

Neodymium titanate was prepared by the following procedure. Neodymium oxide (33.7 grams of $Nd_2O_3$, 0.100 moles) was slowly dissolved in concentrated nitric acid (40 ml) and then heated gently whilst stirring to effect total dissolution. The solution was then boiled to dryness. One half (by weight) of the solid obtained and titanium alkoxide (14.8 grams of $Ti(OR)_4$ where R=$^i$Pr (80%), R=$^n$Bu (20%), 0.0501 moles) were dissolved in methanol (115 ml) and the solution added rapidly to a vigorously stirred ammonia solution (100 ml 28% w/w $NH_3$ in 600 ml deionised water) over 5 minutes and the mixture stirred for a further 30 minutes at room temperature. The resulting mixture was centrifuged, the precipitate was resuspended in methanol (600 ml) which had been treated with 1–2ml of ammonia solution and re-centrifuged.

Figure 18:
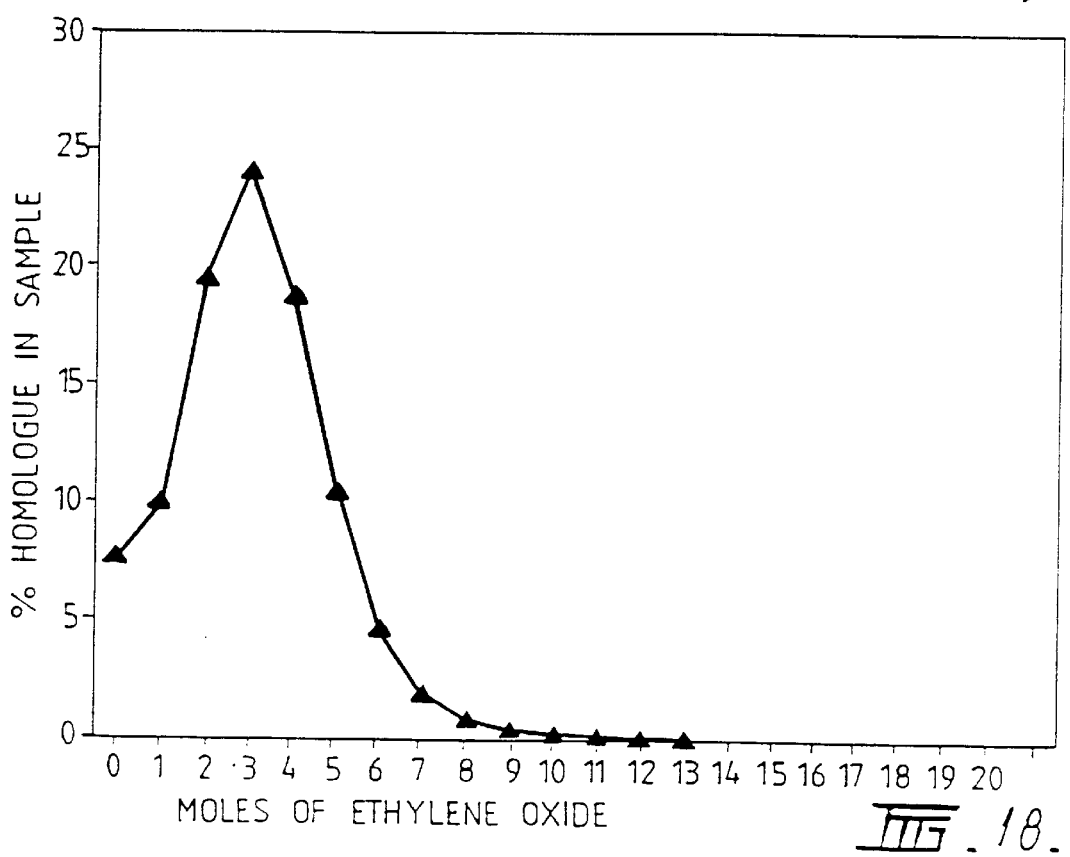

The solid was dried initially in a vacuum oven at 80° C. for 1 hour, then in a furnace at 400° C. for 8 hours. An alkoxylation process in accordance with the invention was conducted under the same general procedures described for Example 1, using as alkoxylation catalyst the neodymium titanate prepared as described above. A total of 253 grams of NACOL-10-99 alcohol and 6.00 grams of neodymium titanate were used. At a reaction temperature of 160° C., a total of 230 grams of ethylene oxide was taken up over 5 hours 45 minutes. The product was analysed by GLC techniques and found to have an average adduct number of 3.2. The ethylene oxide adduct distribution of the product is presented in FIG. 18.

strontium hydroxide (13.7 grams, 0.0500 moles) in deionised water (1000 ml) at 50° C.

The resulting mixture was heated at 50° C. for an additional one hour, the white precipitate allowed to settle and the supernatant liquid decanted. The precipitate was washed with deionised water several times and dried at 400° C. for 18 hours.

Figure 19:
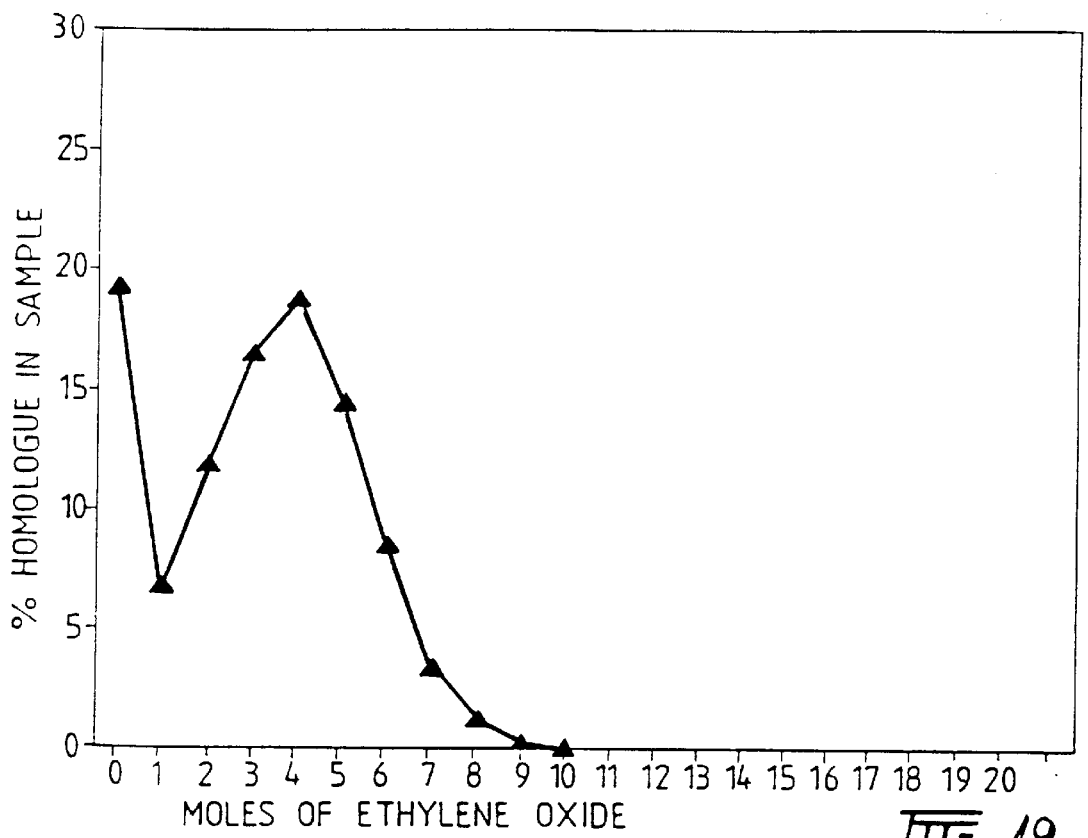

An alkoxylation process in accordance with the invention was conducted under the same general procedures described for Example 1, using as alkoxylation catalyst the barium strontium titanate zirconate prepared as described above. A total of 249 grams of NACOL-10-99 alcohol and 5.16 grams of catalyst were used. At a reaction temperature of 150°–160° C., a total of 180 grams of ethylene oxide was taken up over a period of 48 minutes. The product was analysed by GLC technique and found to have an average adduct number of 3.1. The ethylene oxide adduct distribution of the product is presented in FIG. 19.

Figure 20:
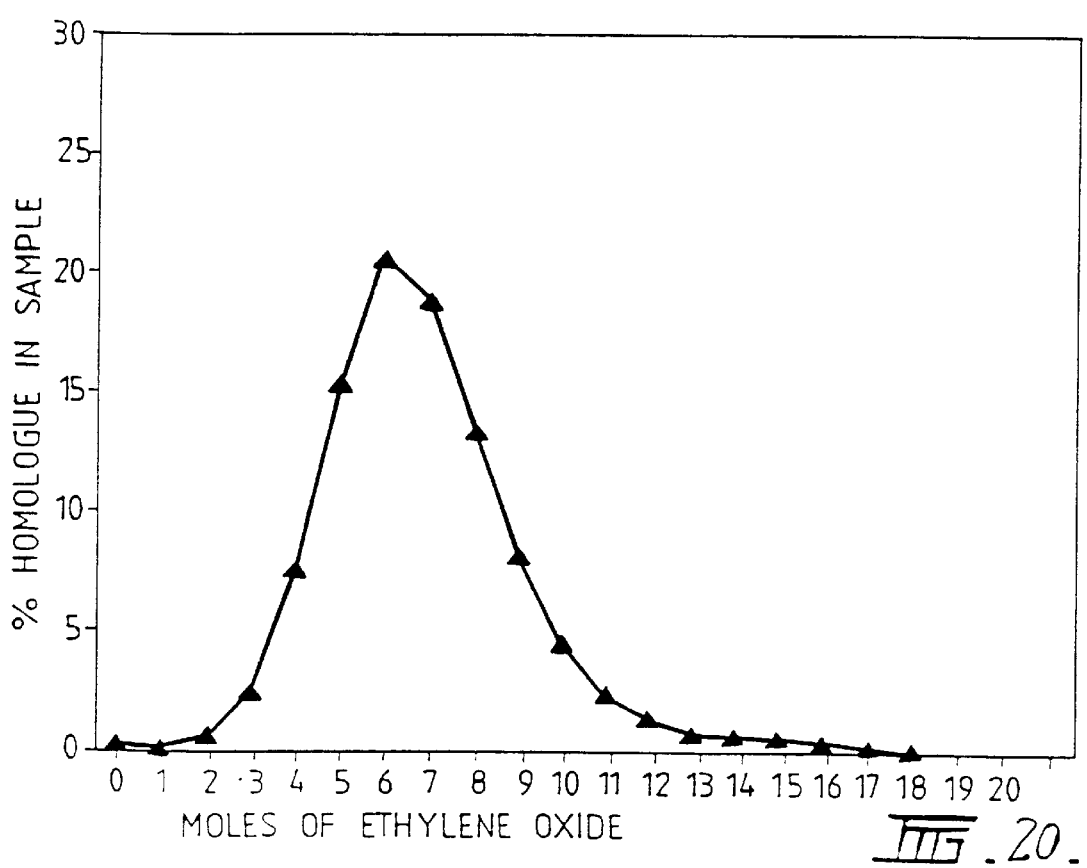

Further alkoxylation of this product (231 grams) was carried out. A total of 175 grams of ethylene oxide was taken up over a period of one hour. The product was analysed by GLC techniques and found to have an average adduct number of 6.8. The ethylene oxide adduct distribution of the product is presented in FIG. 20.

EXAMPLES 13–22

Catalysts in examples 13–22 were prepared in a similar manner to the procedures described in Examples 1–12.

TABLE

Examples 13–22

| Example No | M$^{(a)}$ | X$^{(a)}$ | Molar Ratio M:X$^{(d)}$ | Cat Loading % w/w$^{(e)}$ | Alkoxylation Time h/mol EO$^{(f)}$ | AV EO | Free Alcohol | 1–3 EO | 4–6 EO | 7–15 EO | 16 20 EO |
|---|---|---|---|---|---|---|---|---|---|---|---|
| 13 | Ca/Sr$^{(b)}$ | Ti | 1:1 | 2.5 | 1.4 | 2.8 | 15.0 | 50.0 | 32.5 | 2.5 | — |
|  |  |  |  |  | 2.4 | 5.7 | 1.4 | 11.5 | 56.0 | 30.9 | 0.2 |
| 14 | Mg/Ba$^{(b)}$ | Ti | 1:1 | 2.4 | 3.2 | 2.3 | 19.8 | 54.9 | 24.0 | 1.3 | — |
| 15 | Ca/Ba$^{(b)}$ | Ti | 1:1 | 2.5 | 4.1 | 1.7 | 29.6 | 57.0 | 13.1 | 0.3 | — |
| 16 | Mg | Ti | 1:1 | 1.2 | 7.1 | 1.8 | 23.7 | 64.3 | 12.0 | — | — |
| 17 | K/Ce$^{(c)}$ | Ti | 4:1 | 1.7 | 2.5 | 2.5 | 20.6 | 50.4 | 23.6 | 5.4 | — |
| 18 | Sr/Ba$^{(b)}$ | Zr | 1:0.9 | 2.5 | 0.8 | 3.2 | 16.9 | 41.2 | 33.9 | 8.0 | — |
|  |  |  |  |  | 0.8 | 7.2 | 0.3 | 2.8 | 41.3 | 54.6 | 1.0 |
| 19 | Sr | Zr | 1:0.9 | 2.3 | 1.1 | 3.0 | 16.0 | 46.0 | 32.8 | 5.2 | — |
|  |  |  |  |  | 1.9 | 6.4 | 0.6 | 3.6 | 50.4 | 45.4 | — |
| 20 | Ba | Nb | 1:2 | 4.2 | 2.7 | 2.6 | 15.9 | 55.8 | 25.8 | 2.5 | — |
|  |  |  |  |  | 2.5 | 4.7 | 9.2 | 18.5 | 51.6 | 20.7 | — |
| 21 | Ca | Nb | 1:2 | 3.2 | 2.8 | 2.0 | 29.7 | 50.0 | 18.8 | 1.5 | — |
| 22 | La | Mo | 1:1 | 3.1 | 0.2 | 3.4 | 16.7 | 35.3 | 38.6 | 9.4 | — |
|  |  |  |  |  | 0.3 | 8.1 | 0.8 | 2.6 | 22.0 | 73.9 | 0.7 |

$^{(a)}$Values of M and X in Formula I
$^{(b)}$Molar ratio of the two components of M was 1:1
$^{(c)}$Molar ratio of K:Ce was 4.5:1
$^{(d)}$Molar ratio of M:X as used in catalyst preparation
$^{(e)}$Catalyst loading expressed as % w/w based on alcohol
$^{(f)}$Alkoxylation conducted under the same general procedures described for Example 1

EXAMPLE 12

Barium strontium titanate zirconate was prepared by the following procedure. A solution of tetrabutyltitanate (15.3 grams, 0.0450 moles) and tetrabutylzirconate (20.6 grams, 0.0450 moles) in isopropanol (150 ml) was added dropwise over 70 minutes to a well stirred solution of barium hydroxide (15.9 grams of $Ba(OH)_2.8H_2O$, 0.0500 moles) and

COMPARATIVE EXAMPLE 1

The procedure of Example 1 was repeated substituting 1.68 grams of potassium hydroxide for the barium titanate.

Figure 9:
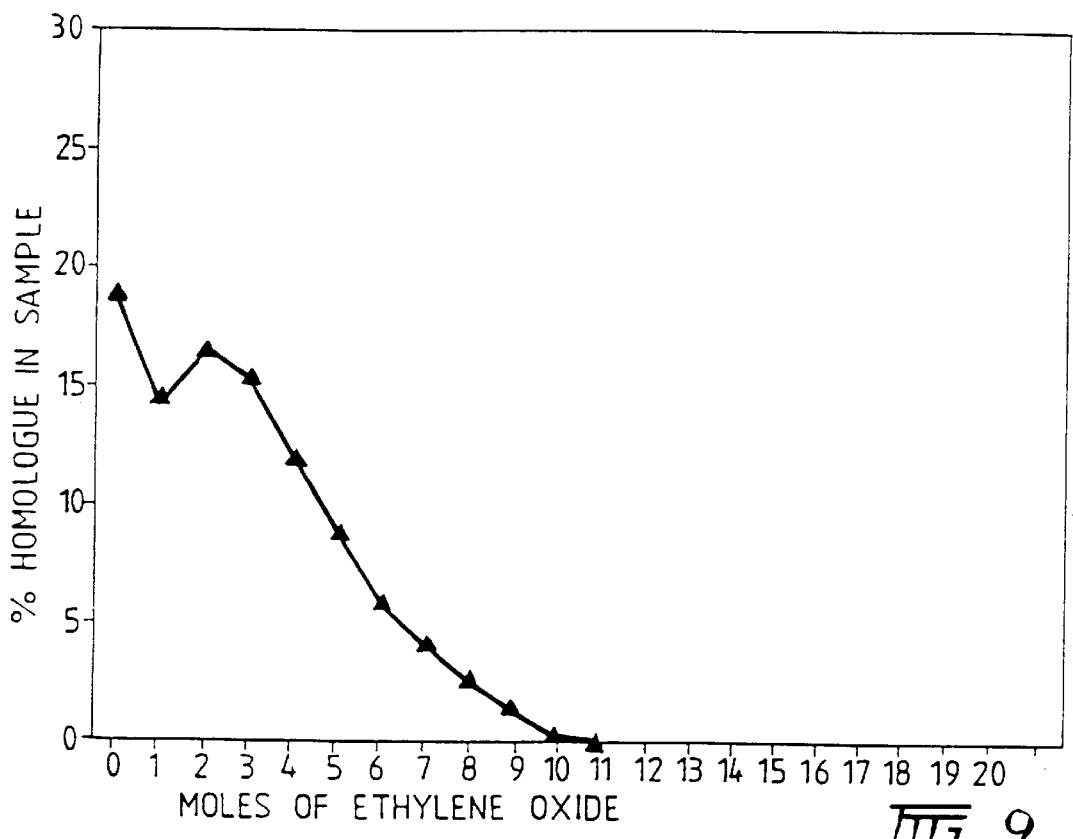

The ethylene oxide was taken up over 20 minutes. The product was analysed by GLC techniques and found to have an average adduct number of 2.8. The ethylene oxide adduct distribution of the product is presented in FIG. 9. Comparison of the product obtained using the process of the present invention according to Example 1 (see FIG. 1) with that obtained using the prior art process (see FIG. 9) clearly demonstrates that although the average adduct number is similar, the process of the present invention gives a product with a much narrow molecular weight distribution even at low ethoxylate numbers.

Figure 10:
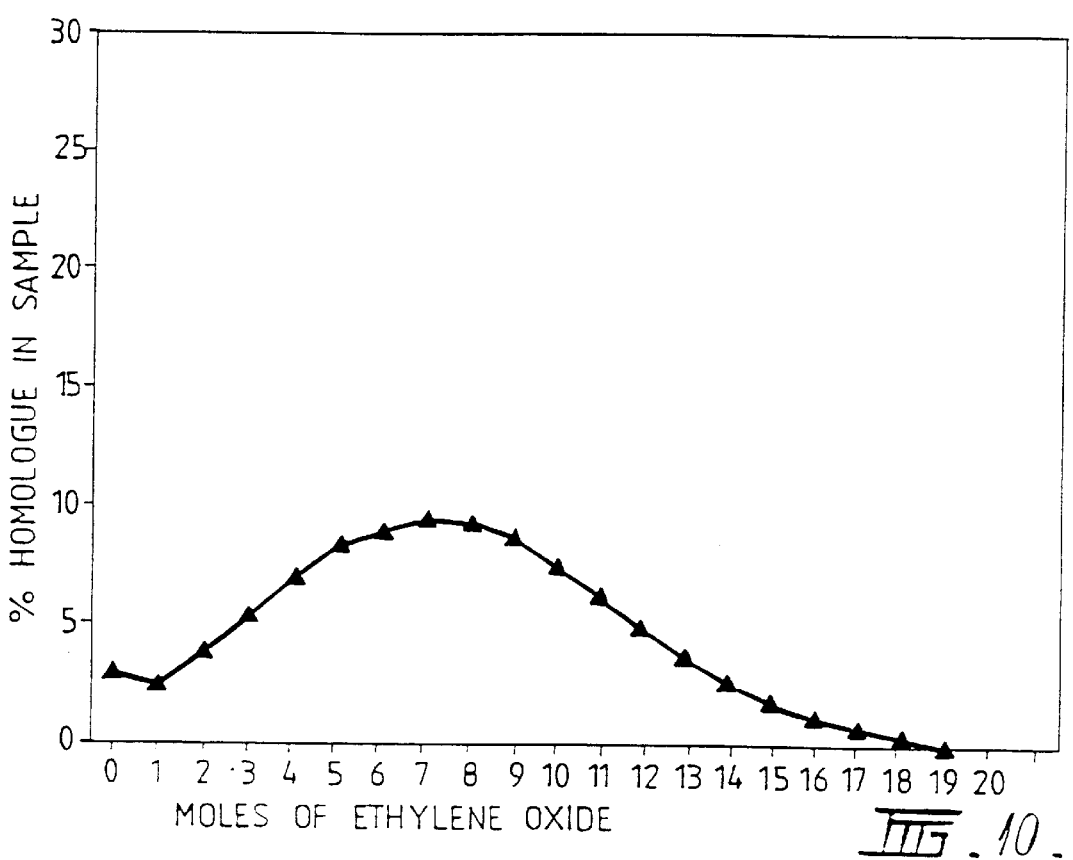

Further ethoxylation of this product was carried out again following the procedure described in Example 1. The ethylene oxide was taken up over 40 minutes. The product was analysed by GLC techniques to have an average adduct number of 7.5. The ethylene oxide adduct distribution of the product is presented in FIG. 10. Comparison of the product obtained according to the process of the present invention and described in Example 1 (FIG. 2) with the product obtained using the prior art process (FIG. 10) clearly illustrates the narrow molecular weight distribution obtained using the process of the present invention.

COMPARATIVE EXAMPLE 2

A process was carried out under the same procedures and conditions of Example 6 except for the use of a lanthanum oxide catalyst in place of the lanthanum titanate catalyst. This process catalysed by lanthanum oxide does not come within this invention and is provided only to illustrate distinction between the invention and lanthanum oxide with respect to catalytic activity.

Lanthanum oxide was prepared as follows:

Ammonia solution (28% w/w, 450 ml) was added over 1.5 hours to a vigorously stirred solution of lanthanum nitrate (89.0 grams of $La(NO_3)_3.5H_2O$, 0.214 moles) in deionised water (1400 ml) at 50° C. The mixture was then stirred for a further one hour at 50° C., cooled and filtered. The precipitate was washed with deionised water and dried at 400° C. for 16 hours.

In the alkoxylation process, 250 grams of NACOL-10-99 alcohol and 7.13 grams of lanthanum oxide were used. At a reaction temperature of 150°–160° C., less than 40 grams of ethylene oxide was taken up over a period of 4 hours.

The claims defining the invention are as follows.
We claim:

1. A process for alkoxylation of organic compounds containing at least one active hydrogen which process comprises reacting said organic compound with an alkylene oxide in the presence of a catalytically effective amount of a salt of a Group Ia or Group IIa element and an oxy acid of at least one element chosen from a Group IVb, Group Vb or Group VIb element or mixtures thereof.

2. A process for alkoxylation of organic compounds containing at least one active hydrogen which process comprises reacting said organic compound with an alkylene oxide in the presence of a catalytically effective amount of a salt of at least one element chosen from a Group Ia or Group IIa or rare earth element and an oxy acid of at least one element chosen from a Group IVb, Group Vb or Group VIb elements or mixtures thereof.

3. A process for alkoxylation of organic compounds according to claim 1 wherein said catalyst is selected from compounds of the general formula:

$$M_m(XO_n)$$

wherein
M is selected from the group consisting of Li, Na, K, Mg, Ca, Sr, and Ba;
X is selected from the group consisting of Ti, Zr, Hf, Nb, Mo, and W;
and m and n are selected to satisfy valency requirements.

4. A process for alkoxylation of organic compounds according to claim 2 wherein said catalyst is selected from compounds of the general formula:

$$M_m(XO_n)$$

wherein
M is selected from the group consisting of Li, Na, K, Mg, Ca, Sr, Ba, Sc, Y, La and mixtures thereof;
X is selected from the group consisting of Ti, Zr, Hf, Nb, Mo, W and mixtures thereof;
and m and n are selected to satisfy valency requirements.

5. A process for alkoxylation of organic compounds according to claim 2 wherein said catalyst is selected from compounds of the general formula:

$$M_m(XO_n)$$

wherein
M is selected from the group consisting of Li, Na, K, Mg, Ca, Sr, Ba, Sc, Y, La, Ce, Nd and mixtures thereof;
X is selected from the group consisting of Ti, Zr, Hf, Nb, Mo, W and mixtures thereof;
and m and n are selected to satisfy valency requirements.

6. A process according to claim 3 wherein n is from 2.0 to 6.0 and m is from 0.2 to 2.0.

7. A process according to claim 3 wherein n is 3 or 4 and m is 1 or 2.

8. A process according to claim 3 wherein M is chosen from the group consisting of Ca, Sr and Ba.

9. A process according to claim 4 wherein M is chosen from the group consisting of K, Ca, Sr, Ba, La and mixtures thereof.

10. A process according to claim 4 wherein M is chosen from the group consisting of K, Ca, Sr, Ba, La, Y, Nd and mixtures thereof.

11. A process according of claim 3 wherein X is chosen from the group consisting of Ti and Sr.

12. A process according to claim 4 wherein X is chosen from the group consisting of Ti, Zr, Hf and mixtures thereof.

13. A process according to claim 4 wherein X is chosen from the group consisting of Ti, Zr, Hf, Mo, Nb and mixtures thereof.

14. A process according to claim 13 wherein said catalyst is chosen from barium titanate, barium zirconate, strontium titanate, strontium zirconate and barium strontium titanate.

15. A process according to claim 4 wherein said catalyst is chosen from lanthanum titanate, potassium lanthanum titanate, yttrium titanate, lanthanum zirconate and lanthanum hafnate.

16. A process according to claim 4 wherein said catalyst is chosen from barium strontium titanate zirconate, barium niobate, lanthanum molybdate and neodymium titanate and calcium titanate.

17. A process according to claim 16 wherein said alkylene oxide is selected from the group consisting of ethylene oxide, epichlorohydrin, propylene oxide, butylene oxide, glycidol, cyclohexene oxide, cyclopentene oxide and styrene oxide.

18. A process according to claim 17 wherein the alkylene oxide is selected from the group consisting of ethylene oxide, propylene oxide and mixtures thereof.

19. A process according to claim 18 wherein said organic compound is chosen from the group consisting of alcohols, thiols, phenols, thiopenols, carboxylic acids, amides and amines.

20. A process according to claim 19 wherein said alcohol is chosen from the group consisting of primary and secondary $C_1$ to $C_{30}$ straight and branched chain alcohols, cycloaliphatic alcohols, glycols, polyethylene glycols, polypropylene glycols and polyhydric alcohols.

21. A process according to claim 20 wherein the level of catalyst used is in the range of from 0.1 percent to 10 percent by weight based on the weight of the organic compound containing reactive hydrogen.

22. A process according to claim 11 wherein the level of catalyst used is from 0.1 percent to 5% by weight of the organic compound containing reactive hydrogen.

23. A process for alkoxylation of organic compounds according to claim 1 comprising the steps of:

adding said catalyst to said organic compound containing at least one active hydrogen;

heating and pressurising a reactor containing said organic compound.

supplying alkylene oxide to said organic compound and catalyst at a process temperature of between 50° and 250° C. and at a pressure of between 300 and 700 kPa and isolating the alkoxylation products.

24. A process according to claim 23 wherein said reaction temperature is between 80° and 200° C.

25. A process according to claim 23 wherein said reaction pressure is between 100 and 500 kPa.

* * * * *